United States Patent [19]

Chamness

[11] Patent Number: 5,702,694
[45] Date of Patent: Dec. 30, 1997

[54] COMPOSITIONS FOR TREATING CORNS, CALLUSES AND WARTS

[75] Inventor: Thomas W. Chamness, Memphis, Tenn.

[73] Assignee: Schering-Plough HealthCare Products, Inc.

[21] Appl. No.: 596,219

[22] PCT Filed: Aug. 11, 1994

[86] PCT No.: PCT/US94/08315

§ 371 Date: Feb. 12, 1996

§ 102(e) Date: Feb. 12, 1996

[87] PCT Pub. No.: WO95/05156

PCT Pub. Date: Feb. 23, 1995

Related U.S. Application Data

[63] Continuation-in-part of Ser. No. 107,553, Aug. 17, 1993.

[51] Int. Cl.$^6$ .................... A61K 7/135; A61K 31/34; A01N 43/04; A01N 25/00
[52] U.S. Cl. .................... 424/78.03; 424/62; 424/69; 424/240; 514/861; 514/24; 514/771; 514/863; 514/887
[58] Field of Search ................ 424/62, 69, 240, 424/78.03; 514/861, 863, 887, 24, 771

[56] References Cited

U.S. PATENT DOCUMENTS

| | | | |
|---|---|---|---|
| 3,856,934 | 12/1974 | Kligman | 514/544 |
| 4,568,539 | 2/1986 | Ashton et al. | 424/69 |
| 4,694,021 | 9/1987 | Schweiger | 424/62 |
| 5,310,730 | 5/1994 | Fujinuma et al. | 514/35 |

FOREIGN PATENT DOCUMENTS

| | | |
|---|---|---|
| A 0273202 | 7/1988 | European Pat. Off. |
| WOA 88 01509 | 3/1988 | WIPO |
| WOA 88 03805 | 6/1988 | WIPO |

OTHER PUBLICATIONS

Patent Abstracts of Japan, vol. 11, No. 251, (C-440) and JP,A, 62 056 411, "Beautifying Agent" (Suzuki Yumiko et al (abstract), 12 Mar. 1987, Japan.

Database WPI Week 8539, Derwent Publications Ltd., London GB 85-239345 and JP,A,60 155 111 (Hisamitsu Pharm KK) (abstract), 15 Aug. 1985, Great Britain, Japan.

Journal of the American College of Toxicology, vol. 5, No. 3, 1986, pp. 123-165.

CA 116(3): 15811c, "Methods of Treating Tumors With Compositions of Catecholic Butanes. . ." (1991).

CA Abstract #91: 9505e of Belgium 871, 192 (1979) Knood Henri.

CA Abstract #113: 178100 of Teikyo Igakac Zosshi (1990), 13(1), 33–41; Nishitani, et al.

Callus and Wart Remover, vol. 91, 1979.

*Primary Examiner*—Thurman K. Page
*Assistant Examiner*—Kathryne E. Shelborne
*Attorney, Agent, or Firm*—Matthew Boxer; John Maitner

[57] ABSTRACT

Topical compositions for the treatment of corns, calluses and warts comprising a benzenediol or a substituted 1,2-benzenediol and a pharmaceutically acceptable carrier, are described.

12 Claims, No Drawings

COMPOSITIONS FOR TREATING CORNS, CALLUSES AND WARTS

The present application is the United States national application corresponding to international Application No. PCT/US 94/08315, filed Aug. 11, 1994 and designating the United States, which PCT application is in turn a continuation-in-part of U.S. application Ser. No. 08/107553, filed Aug. 17, 1993, the benefit of which applications are claimed pursuant to the provisions of 35 U.S.C. 120, 363 and 365 (C).

BRIEF SUMMARY OF THE INVENTION

The invention relates to topical compositions for treating corns, calluses, and warts which comprise a benzenediol. Included among benzenediols are benzenediols or substituted benzenediols selected from the group consisting of hydroquinone, olivetol, pyrocatechol, 2,5-dihydroxy benzoic acid; or 1,2-benzenediols substituted in the 4-position selected from the group consisting of nordihydroguaiaretic acid (NDGA) and 4-nitrocatechol, in combination with a pharmaceutically acceptable carrier. The invention also relates to a method for treating the above-described conditions which comprises administering an effective amount of a benzenediol or substituted benzenediol selected from the group consisting of hydroquinone, olivetol, pyrocatechol, and 2,5-dihydroxy benzoic acid or 1,2-benzenediols substituted, for example, on the 4-position, such as nordihydroguaiaretic acid (NDGA) and 4-nitrocatechol.

DETAILED DESCRIPTION OF THE INVENTION

Hyperkeratotic tissues, such as: corns (heloma), calluses (tyloma) and warts (condyloma), are well defined, thickened lesions of the epidermis. They occur at skin sites that are normally involved in chronic mechanical stress (corns and calluses) or infected with papilloma virus (warts). Pain produced by the thickened tissue can cause these lesions to be debilitating.

Traditionally, "keratolytic agents", such as: salicylic acid and resorcinol, have been applied topically to these lesions to solubilize intercellular bonds resulting in desquamation of the thickened, hyperkeratotic tissues.

The goal was to develop a faster acting corn and callus remover product. To achieve this goal benzenediols were evaluated. Assays of keratinocyte differentiation and keratolytic action, as described below were employed to identify the compounds that possess this activity.

As used herein, "alkyl" means a straight or branched chain alkyl group. Alternatively, the number of carbon atoms in a particular alkyl group may be specified. For example, $C_1$–$C_8$ alkyl, refers to a straight or branched chain alkyl group having one to eight carbon atoms. Halo refers to chloro, bromo, iodo, and fluoro.

The present invention provides new topical compositions for the treatment of all kinds of corns, calluses, or warts. The compositions of the invention provide for faster removal of corns, calluses, and warts than do prior art compositions. The compositions of the invention can also be used in the treatment of hyperkeratinizing and hyperproliferative skin diseases and conditions such as ichthyoses, porokeratoses, follicular keratoses, palmoplantar keratodermas, psoriasis, eczema, dandruff and dry skin. The invention also relates to a method for treating the above-described medical conditions which comprises administering an effective amount of a benzenediol or substituted benzenediol selected from the group consisting of hydroquinone, olivetol, pyrocatechol, 2,5-dihydroxy benzoic acid; or a 1,2-benzenediol substituted in the 4-position selected from the group consisting of nordihydroguaiaretic acid (NDGA) and 4-nitrocatechol.

The topical compositions of the present invention comprise a benzenediol. As used herein, "benzenediol" means the following: a benzenediol or a substituted benzenediol. Among substituted benzenediols are dihydroxyphenylalkyl benzenediols. Exemplary of benzenediols and substituted benzenediols are compounds such as hydroquinone, olivetol, pyrocatechol, 2,5-dihydroxy benzoic acid; or a 1,2-benzenediol substituted, for example, in the 4-position. More specifically, the substituents which can occur in the 4-position or in other positions on the benzene in the compounds of the invention are nitro, halo, $C_1$–$C_8$ alkyl, or dihydroxyphenyl-$C_1$–$C_8$ alkyl-. Specific 1,2-benzenediols substituted in the 4-position include nordihydroguaiaretic acid (NDGA) and 4-nitrocatechol.

A preferred benzenediol of the invention is pyrocatechol.

Pyrocatechol is a 1,2-benzenediol. The chemical structure of pyrocatechol is as follows:

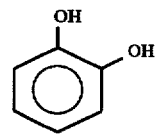

Pyrocatechol is a crystalline compound with a phenolic odor. Pyrocatechol has several industrial applications and has been used in the past as a topical antiseptic (Merck Index, 11th Edition, 1989, S. Budavari, Editor, Merck and Company, Rahway, N.J., page 1272). The antiseptic properties of pyrocatechol derive from its relatedness to phenol. Pyrocatechol has been used in hair dye at concentrations of ≦1% (Final Report on the Safety Assessment of Hydroquinone and Pyrocatechol, 1986, Journal of American College of Toxicology, 5:123–165).

A more preferred 1,2-benzenediol substituted in the 4-position is nordihydroguaiaretic acid (NDGA), a substituted 1,4-benzenediol, which has the following structure:

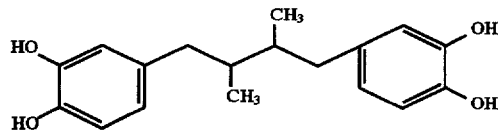

NDGA is a crystalline, odorless powder. It is used as an antioxidant in fats and oils (Merck Index, 11th Edition, 1989 S. Budavari, Editor, Merck Company, Rahway N.J., Pages 1057–1058).

The topical compositions of the invention also comprise a pharmaceutical carrier material suitable for topical use.

A composition in accordance with the invention comprises a benzenediol in a range of about 2 to about 64% (weight/weight).

More specifically, the topical compositions of the invention contain a benzenediol or substituted benzenediol selected from the group consisting of hydroquinone, olivetol, pyrocatechol, 2,5-dihydroxy benzoic acid; or a 1,2-benzenediol substituted in the 4-position selected from the group consisting of nordihydroguaiaretic acid (NDGA) and 4-nitrocatechol, at a range of about 2 to about 64% (weight/weight). A preferred range for pyrocatechol or NDGA is about 3 to about 24% (weight/weight). As used herein, the term "weight/weight" means the ratio of the weight of the particular ingredient in question to the weight of the entire composition.

Those skilled in the art will be able to maximize the safety and efficacy of a given formulation. Compositions of the invention can take any of the following delivery forms: salves, lotions, plaster devices, collodion-type vehicles, suspensions, ointments, creams, gels, sprays, bandages, patches or other appropriate topical vehicles or delivery devices.

Topical compositions of the invention contain a pharmaceutically acceptable carrier. The pharmaceutically acceptable carrier delivers the active ingredient to the site of application. The pharmaceutically acceptable carrier may be a liquid such as glycol, petrolatum, ethanol, acetone, dimethyl sulfoxide (DMSO), and the like. The pharmaceutically acceptable carrier may also be pad devices, disks or plaster. The pharmaceutically acceptable carrier may also be a film former such as flexible collodion, USP.

Topical compositions of the invention may also contain a viscosity enhancer. Viscosity enhancers increase the viscosity of the composition so that it does not spread beyond the site of application. An example of a viscosity enhancer is Balsam Fir (Oregon).

Topical compositions of the invention may also contain a film former. When a film former dries, it forms a protective film over the site of application to prevent removal of active ingredient from the site. An example of a film former which may be used is Flexible Collodion, USPTopical compositions of the invention may also contain a colorant such as β-Carotene. Topical compositions of the invention may also contain a solvent which serves to dissolve the active ingredient. An example of a solvent which may be used is acetone. As can be seen, the solvent may also sometimes serve as the carrier.

In preparing topical compositions of the invention, there can be added conventional adjuvants such as propionic acid, propylene glycol, acetone and lactic acid, conventional penetration enhancers such as erucic acid, oleic acid, and behenic acid; conventional buffers, preservatives, hydrophilic emulsifiers, lipophilic emulsifiers, sun-screening agents, perfumes, emollients, deodorants, humectants, and the like. Colorants may also optionally be added in the compositions of the invention.

Current collodion-based FDA monograph approved formulas may be employed in such topical liquid compositions.

One skilled in the art, would be able to devise other suitable liquid formulations.

Alternatively, current plaster pad-type FDA monograph approved formulas may be used in devising compositions of the invention.

One skilled in the art would be able to devise a variety of suitable plaster pad-type formulations. Modified FDA monograph approved pad devices, disks or plaster may also be used as the carrier material. One skilled in the art would be able to apply benzenediols to these pad devices, disks or plaster to form a composition of the invention.

Modified FDA monograph approved liquid vehicles may be used as the carrier material.

In preparing topical compositions of the invention, there can be added conventional adjuvants such as propionic acid, salicylic acid, propylene glycol, acetone and lactic acid, conventional penetration enhancers such as erucic acid, oleic acid, and behenic acid; conventional buffers, preservatives, hydrophilic emulsifiers, lipophilic emulsifiers, sun-screening agents, perfumes, emollients, deodorants, humectants, and the like.

In applying liquid formulations to the patient in need of such treatment, liquid formulations are applied, rubbed or spread on the affected area of the skin. In applying plaster-pad formulations to the patient in need of such treatment, plaster-pad formulations are applied to the affected area of the skin so that the pad adheres to the skin.

In preparing topical compositions of the invention which contain NDGA, there can be added conventional adjuvants such as propionic acid, salicylic acid, propylene glycol, acetone and lactic acid, conventional penetration enhancers such as erucic acid, oleic acid, and behenic acid; conventional buffers, preservatives, hydrophilic emulsifiers, lipophilic emulsifiers, sun-screening agents, perfumes, emollients, deodorants, humectants, and the like. Colorants may also optionally be added in the compositions of the invention.

Compositions of the invention are to be applied in a therapeutically effective amount. A "therapeutically effective amount" means any amount which will cause improvement in a disease condition (such as removal of a callus) when applied to the affected area repeatedly over a period of time. The amount will vary with the condition being treated and the concentration of the active ingredients in the formulation being applied. Appropriate amounts in any given instance will be readily apparent to those skilled in the art by routine experimentation.

Experiments were carried out which demonstrate that when a benzenediol such as pyrocatechol or NDGA is included in compositions, that the resulting composition is more effective in causing callus sloughing from guinea pig footpads, than salicylic acid alone. These experiments are described below.

Action of Pyrocatechol, NDGA or SA in Removal of Guinea Pig Footpad Callus: Description of Guinea Pig Footpad Assay (GPFA)

To evaluate keratolytic agents an animal model, GPFA, was developed. The analysis was performed according to the following protocol, using the guinea pig footpad as the test site. Three Hartley guinea pigs (250–400 g) were used per test group for in vivo evaluations. Either right or left footpads were treated with the opposite footpad as untreated control. For each treatment group, the same footpad was treated on each animal. The treated footpad received 200 μl of the test material saturated into a small cotton pledget. The cotton pledget was occluded with several wrappings of Blenderm tape (3m Corporation, St. Paul, Minn.) and finally secured from removal with a wrapping of Zonas tape (Johnson and Johnson, New Brunswick, N.J.). Each group of three animals was placed in a polycarbonate cage with contact bedding for 18–24 hours (overnight). At the end of the treatment period, the bandages were removed with surgical scissors and the footpads were examined for gross keratolytic effects or dermatotoxicity. Observations were carried out at daily intervals for one week. Clinical grades were recorded for possible keratolytic effects beginning on Day 2 and continuing through Day 7. Appropriate vehicle controls and bandage control groups were included in each experiment. Pyrocatechol (Sigma Chemical Company, St. Louis, Mo.) and NDGA (Aldrich Chemical Co., Milwaukee Wis.) were prepared as a 12% (weight/weight) solution as described below. SA was prepared as a 12.6% (weight/weight) solution as described below.

| Liquid Formulas for Evaluating Pyrocatechol and NDGA in the GPFA. | |
|---|---|
| Component | Percentage of Formula % (weight/weight) |
| Pyrocatechol or NDGA | 12.0 |
| Balsam Fir (Oregon) | 5.0 |
| β-Carotene, 22% in Vegetable Oil | 0.05 |
| Acetone | 10.0 |
| Flexible Collodion, USP | q.s. 100.0 |

The pyrocatechol formula in the preferred vehicle was prepared as follows:

1) Balsam fir (Oregon) was mixed with acetone in a suitable vessel.
2) β-Carotene, 22% in vegetable oil, was added to the solution prepared in step 1 and thoroughly mixed.
3) Flexible collodion, USP, was added to the solution prepared in step 2 and thoroughly mixed.
4) Pyrocatechol was added to the solution prepared in step 3.
5) The composition from step 4 was thoroughly mixed until the pyrocatechol was completely dissolved.
6) The composition made in step 5 was then transferred to appropriate containers for storage at room temperature ranging from about 22° to about 27° C.

NDGA was formulated in the preferred vehicle in the same manner as pyrocatechol shown just above.

| Liquid Formula for Evaluating SA in the GPFA. | |
|---|---|
| Component | Percentage of Formula % (weight/weight) |
| SA | 12.6 |
| Balsam Fir (Oregon) | 5.0 |
| β-Carotene, 22% in Vegetable Oil | 0.05 |
| Acetone | 10.0 |
| Flexible Collodion, USP | q.s. 100.0 |

1) Balsam fir (Oregon) was mixed with acetone in a suitable vessel.
2) β-Carotene, 22% in vegetable oil, was added to the solution prepared in step 1 and thoroughly mixed.
3) Flexible collodion, USP, was added to the solution prepared in step 2 and thoroughly mixed.
4) SA was added to the solution prepared in step 3.
5) The composition from step 4 was thoroughly mixed until the pyrocatechol was completely dissolved.
6) The composition made in step 5 was then transferred to appropriate containers for storage at room temperature ranging from about 22° to about 27° C.

The relative efficacy of keratolytic action of the compounds for removal of guinea pig foot pad callus was determined by the following clinical grading scale:

| Clinical Grade | Appearance of Footpad and Footpad Callus |
|---|---|
| 0 = | No visible difference, smooth feet, or equivalent to control. |
| 0.5 = | Slight fine cracks in skin visibly different from control. |
| 1 = | Somewhat larger cracks with edges turned up slightly. |
| 2 = | Obvious separation of stratum corneum (SC) over a limited area of the footpad. |
| 3 = | Separation of SC over a large area of the footpad. |
| 4 = | SC has peeled off completely revealing intact underlying epidermis, i.e., normal appearing skin. |

The clinical grades were then used to calculate a keratolytic efficacy score referred to as the Keratolytic Index (KI). The following formula is used to calculate the KI for a given test group.

$$KI = \frac{\text{Maximum Average Clinical Grade}}{\text{The Number of Days Until The Average Clinical Grade} \geq 2} \times 10$$

The KI scores achievable for this analytical method range from 0, no apparent keratolytic activity, to 20, maximum keratolytic action. The results of a typical GPFA comparing the KI of pyrocatechol with that of SA is given in Table 1 below. Pyrocatechol KI (11.1) and NDGA KI (6.7) both have a higher index score than salicylic acid (4.4) under these test conditions. The average KI in control groups was less than 1. There was no evidence of dermatotoxicity caused by pyrocatechol, NDGA or SA in any of the assays that were conducted.

TABLE 1

Table 1: KI for Pyrocatechol, NDGA and SA Determined in the GPFA.

| Treatment Group | (N) | Average Daily Clinical Grades | | | | | | KI |
|---|---|---|---|---|---|---|---|---|
| | | Day-2 | Day-3 | Day-4 | Day-5 | Day-6 | Day-7 | |
| SA (12.6%) | 3 | 0.3 | 0.6 | 1.3 | 1.7 | 2.3 | 2.7 | 4.4 |
| Pyrocatechol (12%) | 3 | 0.8 | 2.0 | 2.3 | 3.0 | 3.0 | 3.3 | 11.1 |
| NDGA (12%) | 3 | 1.3 | 1.7 | 2.3 | 2.7 | 2.7 | 2.7 | 6.7 |

Effects of Pyrocatechol, NDGA and SA on Cell Proliferation and Protein Synthesis The following experimental protocol was used to determine whether pyrocatechol or SA had any effect on the rate of cell proliferation or protein synthesis by cultured NHEK cells. A separate experiment was conducted to determine if NDGA had any effect on cell proliferation. NHEK cells are grown in monolayers in 6 well plastic tissue culture plates in serum free KGM Medium (Clonetics) until confluency of approximately 80% was achieved. To culture the cells, the plates were placed in a humidified, 5% $CO_2$ incubator at 37°

C. To the cells were added various concentrations of either SA, pyrocatechol, or NDGA with appropriate controls, for 18 hours (overnight). Simultaneous with this treatment, 1 µCi/ml each of $^{35}$S-methionine (protein precursor) and $^3$H-thymidine (DNA precursor) were added to the cells. For NDGA group, the cells were treated with $^3$H-thymidine only. Following the treatment phase, the cells were washed, harvested and counted in a liquid scintillation counter (triplicate wells/treatment group) to determine the levels of incorporation of the radiolabeled precursors into cellular DNA and protein. The level of radioactivity recovered in the cells is a measure of cells proliferation and protein synthesis.

The results of these experiments are shown in Tables 2, 3 and 4. As used in Tables 2, 3 and 4, DPM means disintegrations per minute.

TABLE 2

Effects of SA on DNA and Protein Synthesis in NHEK Cells

| Dose | $^3$H-Thymidine DPM ± SD | $^3$H-Methionine DPM ± SD |
|---|---|---|
| SA 10 mM | 26262 ± 18051 | 51611 ± 25175 |
| SA 20 mM | 3012 ± 1721 | 1767 ± 123 |
| SA 30 mM | 820 ± 7.0 | 1794 ± 113 |
| EtOH 0.9% (vehicle) | 264069 ± 34572 | 304993 ± 15662 |
| Untreated (control) | 3906020 ± 82954 | 377252 ± 15662 |

TABLE 3

Effects of Pyrocatechol on DNA and Protein Synthesis in NHEK Cells

| Dose | $^3$H-Thymidine DPM ± SD | $^3$H-Methionine DPM ± SD |
|---|---|---|
| Pyrocatechol 10 mM | 3437 ± 4203 | 12375 ± 9863 |
| Pyrocatechol 20 mM | 890 ± 79 | 5928 ± 19 |
| Pyrocatechol 30 mM | 975 ± 123 | 7837 ± 21246 |
| EtOH 0.9% (vehicle) | 264069 ± 34572 | 304993 ± 21246 |
| Untreated (control) | 3906020 ± 82954 | 377252 ± 15662 |

TABLE 4

Effects of NDGA on DNA synthesis in NHEK cells

| Dose | $^3$H-Thymidine DPM ± SD |
|---|---|
| NDGA 20 mM | 4,867 ± 247 |
| EtOH 0.9% (vehicle) | 93,237 ± 19,382 |
| Untreated (control) | 203,520 ± 536 |

Both SA and pyrocatechol inhibit cell proliferation and protein synthesis in NHEK cells. Under the conditions of these analyses, pyrocatechol was more effective in blocking DNA and protein synthesis than SA. These compounds exhibited strong dose-dependent inhibition of DNA and protein synthesis (≧90% of control values). In a single dose experiment, NDGA also showed strong inhibition of DNA synthesis in a manner similar to pyrocatechol and SA. To show that the effects of pyrocatechol and SA were specific for DNA and protein synthesis and not due to cell death, the viability of the treated cells was determined by a neutral red assay. The results of this assay showed that 80–95% of the treated cells were viable. This activity is an important factor in corn/callus treatment (keratolysis) where hyperplastic growth of the skin is one of the observed pathological changes.

Effects of Pyrocatechol and SA on Intracellular Calcium Levels

An in vitro assay method was employed to measure calcium flux induced by the compounds under investigation. Human squamous carcinoma cells (SCC-9 cell line) were grown to confluent monolayers in 75 cm$^2$ tissue culture flasks at 37° C. in a humidified, 5% $CO_2$ incubator. The cells in each flask were cultured in 15 ml of complete medium, consisting of: Ham's F12 Medium and Dulbecco's Modified Eagle's Medium mixed 1:1 (Gibco Laboratories, Grand Island, N.Y.), 10% fetal bovine serum (Hyclone Laboratories, Logan, Utah), 0.4 µg/ml hydrocortisone, 2 mM L-glutamine, 100 U/ml penicillin, 100 µg/ml streptomycin and 0.25 µg/ml amphotericin B (Sigma). On days that the calcium flux experiments were conducted the cell culture medium was removed and replaced with medium containing 8 µM Indo-1AM (Sigma) and 10 µl/ml pluronic surfactant F-127 (Calbiochem, San Diego, Calif.) and incubated for 1 hour at 37° C. The medium was removed and fresh tissue culture medium was added to the flask and the cells were incubated at 37° C. for 1 hour. The cell monolayer was disrupted and the cells dispersed into a single cell suspension by removing the tissue culture medium, washing the monolayer with phosphate buffered saline (PBS), adding 2.5 ml of trypsin solution (0.5 mg/ml) (Sigma) and incubating for 10 minutes at 37° C. The cells were washed and resuspended in buffer containing 1.5 mM calcium. Test compounds dissolved in 200 proof ethanol were added to cell aliquots and calcium induced Indo-1 fluorescence was measured spectrophotometrically with excitation at 355 nm and emission at 407.6 nm. The results of the experiment are presented in Table 5

TABLE 5

Calcium Flux in SCC-9 Cells

| Compound | Dose | Relative Fluorescence |
|---|---|---|
| (nontreated control) | | 0 |
| SA | 176 µM | 40.56 |
| Pyrocatechol | 176 µM | 8.82 |
| 4BrA23187 (positive control) | 19 µM | 42.32 |

The relative levels of fluorescence (i.e., an indirect measure of intracellular calcium concentration) above nontreated control levels, for cells treated with SA (176 µM) and calcium ionophore 4-Br-A23187 (19 µM) were virtually identical at 40.56 and 42.32, respectively. In comparison, the intracellular calcium concentration in cells treated with 176 µM pyrocatechol was significantly less (relative fluorescence=8.82). The results of this study indicate that SA and pyrocatechol are capable of inducing increased intracellular calcium flux in human keratinocytes (SCC-9 cells). Such activity indicates that SA and pyrocatechol are useful as agents in causing enhanced kerotinocyte differentiation.

Effects of Pyrocatechol and SA on Ultrastructural Localization of Calcium in Normal Human Skin Pieces of full thickness, normal human skin were placed in organ culture with an air/liquid interface at the level of the stratum corneum. The organ culture Medium was as follows: Dulbecco's Modified Eagle's Medium (DMEM); 100 µg/ml, hydrocortisone, hemisuccinate; 2 mM L-glutamine; 300 U/ml penicillin; 30 mg/ml streptomycin; and 0.75 amphotericin B (Sigma). 12.6% (weight/weight) of each test compound was dissolved in the flexible collodion/acetone vehicle described at Example E below of this application and was applied topically to the skin pieces and incubated for 48 hours at 37° C. The skin pieces were then washed and prepared for observation by transmission electron microscopy (TEM). Calcium was precipitated within the tissue by incubating the skin overnight in ice cold fixative (at pH 7.4) consisting of: 2% glutaraldehyde, 2% formaldehyde, 90 mM potassium oxalate and 1.4% sucrose. In the postfixative procedure the skin was incubated for 2 hours at 4° C. in 1% osmium tetroxide and 2% potassium pyroantimonate adjusted to pH 7.4 with acetic acid. The tissues were sectioned and lightly stained with uranyl acetate and mounted on grids for examination using a JOEL 2000 TEM.

The results of this study are described just below.

In nontreated, control skin, the distribution of calcium within a keratinocyte in the stratum spinosum is as follows. Calcium is associated in aggregates that are evenly dispersed throughout the nuclear euchromatin. Calcium is also readily observed in the cytoplasm of this cell and extracellular compartment. At the level of the stratum granulosum, high concentrations of calcium are seen in the extracellular space along the cell borders and in association with the desmosomes. In contrast, calcium is not detected, by this method, in the extracellular compartment, in association with desmosomes or in the cytoplasm of keratinocytes of skin treated with pyrocatechol. High concentrations of calcium are distributed throughout the nuclear heterochromatin of keratinocytes from pyrocatechol treated skin. Evidence of desmosome degradation is also observed in this tissue section. In the stratum spinosum of skin treated with SA the distribution of calcium is similar, but not identical, to that observed in pyrocatechol treated skin. For example, there is very little calcium seen in either the extracellular compartment or associated with desmosomes. Unlike the effect of pyrocatechol, SA treatment did not cause degradation of desmosomes. Calcium in the nuclei of keratinocytes in skin treated with SA is highly concentrated within the heterochromatin. In one section of skin treated with SA, two keratinocytes can be observed. In one keratinocyte calcium is not detected in the euchromatin, in the other keratinocyte calcium is thinly dispersed in the euchromatin. Collectively, these data demonstrate the variable effects of these compounds on calcium localization within the skin. Changes in calcium distribution from the extracellular compartment to the nuclear heterochromatin are linked to enhanced keratinocyte differentiation and desquamation and these studies clearly show that the effect of pyrocatechol≧SA in causing these changes.

Effect of Pyrocatechol, NDGA and SA on the Expression and Distribution of Desmosomal Protein, Desmoglein, in the Epedermis of Organ Cultured Normal Human Skin Immunoperoxidase staining was employed to detect desmoglein (DG) expression in organ cultured skin treated with pyrocatechol, NDGA and SA. Pieces of full thickness normal human skin were placed in organ culture at an air/liquid interface at about the level of the stratum corneum. Test compounds were added to the tissue culture medium at a final concentration of 15 mM. An equal volume of ethanol, which was used as the solvent for the stock test compounds, was added to the medium of the control cultures. The skin pieces were incubated for 24 hours at 37° C. before they were prepared for frozen sectioning. After removal from organ culture the pieces of skin were fixed in O.C.T. Embedding Medium (Tissue-Tek, Miles Laboratories, Inc., Elkhart, Ind.) and frozen in liquid nitrogen. Frozen sections of O.C.T. fixed tissues were cut on a cryostat set to 5 micron thickness and the sections were placed on glass slides. The tissue sections were rehydrated with PBS for 10 minutes at room temperature. To reduce nonspecific antibody binding the tissue sections were covered with normal goat serum (Accurate Chemical and Scientific, Corp., Westbury, N.Y.), diluted 1:20 with PBS, and incubated in a humidified chamber at room temperature for 20 minutes. The tissues were washed with PBS, covered with 100 µl of primary antibody solution and incubated for 2 hours at room temperature. Primary antibodies used in this study were anti-desmoglein (Boehringer Mannheim Biochemicals, Indianapolis, Ind.), a mouse monoclonal IgG 2b antibody raised against human 165 kD DG protein, and normal, nonimmune mouse serum (Aceurate) that served as a nonspecific binding control. The primary antibodies were diluted in PBS at 1:100 for antiDG and 1:500 for normal mouse serum for tissue binding. After binding of the primary antibodies was completed, the tissue sections were washed 3× with excess amounts of PBS. The sections were blotted dry on a paper towel, covered with 100 µl of a secondary antibody, biotin-conjugated goat antimouse IgG (Accurate) diluted 1:100 with PBS, and incubated 20 minutes at room temperature. The sections were washed 3× in excess PBS. They were covered with horseradish peroxidase conjugated streptavidin (Accurate) that was diluted 1:100 in PBS and incubated for 20 minutes at room temperature. The tissue sections were washed 3× in excess amounts of PBS and incubated 3 minutes in AEC solution, consisting of: 20 mg 3-amino-9-ethylcarbazole dissolved in 5 ml dimethylsulfoxide and mixed with 50 µl of hydrogen peroxide (30% solution) in 20 mM acetate buffer at pH 5.2, which results in a reddish precipitate at sites of peroxidase-antibody binding. After washing off the AEC solution with PBS, the tissues were lightly counterstained with hemotoxylin. The sections were washed with PBS and mounted in glycerol under a cover glass for light microscopic examination. The results of this study are described below.

DG is expressed throughout the stratum spinosum layer of control skin, as well as skin treated with SA. In contrast, pyrocatechol treated skin showed no detectable staining for DG protein. This indicates that pyrocatechol is useful as an agent in inducing desquamation. NDGA decreased DG expression determined by stain development to a greater level than SA but not as great as pyrocatechol. NDGA is also a useful agent in inducing desquamation.

These observations are consistent with the observed ultrastructural changes to desmosomes in TEM photomicrographs.

Effects of Pyrocatechol, NDGA and SA on Cross-linked Cellular Envelope Formation An in vitro assay method was used to measure cellular envelope (CE) formation induced in cultured keratinocytes by the three compounds under investigation. Human squamous carcinoma cells (SCC-9 cell line) were grown to confluent monolayers in 25 cm² plastic tissue culture flasks at 37° C. in a humidified, 5% $CO_2$ incubator. The cells in each flask were cultured in 10 ml of complete medium, consisting of: Ham's F12 Medium and Dulbecco's Modified Eagle's Medium mixed 1:1 (Gibco), 10% fetal bovine serum (Hyclone), 0.4 µg/ml hydrocortisone, 2 mM L-glutamine, 100 U/ml penicillin, 100 µg/ml streptomycin and 0.25 µg/ml amphotericin B (Sigma). On days that the CE induction experiments were performed the cell culture medium was removed and the cell monolayer was washed with 20 ml of PBS. The cell monolayers were then covered with 5 ml of Hank's balanced salt solution formulated with 2 mM calcium. A fixed volume from stock solutions were added to each flask to give final concentrations of calcium ionophore A23187 (100 µM), pyrocatechol (15 mM), NDGA (15 mM) and SA (15 mM) (Sigma). All experimental groups were run in triplicate. An equal volume of ethanol, the solvent used to prepare the stock solutions, was added to the flasks designated as controls. The cells were then incubated for 6 hours in a humidified, 5% $CO_2$ incubator at 37° C. A rubber policeman was used to scrape the cells off the surface of the flasks. The cells were transferred to 15 ml plastic centrifuge tubes and pelleted by centrifugation at 800×g for 10 minutes. The supernatants were removed and the cells were resuspended in 1 ml of PBS containing 2% sodium dodecyl sulfate (SDS), 20 mM dithiothreitol and 30 µg DNAase (Sigma) to extract the CE. The CE were dispersed into suspension by placing the tubes in a waterbath sonicator for 10 minutes. They were then placed in a drying oven with the ambient air temperature at 100° C. for 10 minutes. The CE were then sonicated for 10 minutes, an additional 30 µg of DNAase was added and the CE were allowed to cool at room temperature for 10 minutes. The contents of the 15 ml centrifuge tubes were transferred to plastic 1.8 ml microfuge tubes using disposable, glass pasture pipets. The CE were pelletted in a microcentrifuge at 1000×g for 10 minutes at 25° C. The supernatants were discarded and the CE were resuspended in 1 ml of 0.1% SDS in PBS and pelleted at 1000×g for 10 minutes at 25° C. The CE were resuspended in 1 ml of 0.1% SDS in PBS and analyzed by spectrophotometry. Absorption (i.e., light scatter) measurements were made at 340 nm.

The results of this study are presented in Table 6.

TABLE 6

Cellular Envelope Formation in SCC-9 Cells

| Compound | Dose | Absorbance @ 340 nm (mean ± SEM × $10^{-4}$) |
|---|---|---|
| A23187 | 100 µM | 922 ± 119 |
| Pyrocatechol | 15 mM | 9316 ± 323 |
| SA | 15 mM | 566 ± 98 |
| Et OH Control | | 328 ± 14 |

The data are given as the mean±S.E.M. absorption value for each test group. As can be seen, CE were induced by treating the SCC-9 cells with either ionophore A23187 or SA. About twice as many CE were induced by ionophore as were induced by SA. In comparison, about 20 times more CE were induced by pyrocatechol. The studies for NDGA were evaluated using the above method and then counting all cell envelopes in a hemocytometer. The results are as follows:

| Compound | Concentration of cell envelopes in (CE)/ml |
|---|---|
| pyrocatechol (15 mM) | $3.2 \times 10^5$ |
| SA (15 mM) | $0.2 \times 10^5$ |
| NDGA (15 mM) | $1.0 \times 10^5$ |

These data indicate that pyrocatechol and NDGA are both potent stimulators of CE formation in SCC-9 cells compared to the activities of calcium ionophore A23187 and SA. NDGA produced about 5 times the number of CE as SA. A23187 is the antibiotic calcimycin with the formula $C_{29}H_{37}N_3O_6$ which is described on page 249, entry 1639 of Merck Index, 11th Edition, 1989, S. Budavari, Editor, Merck and Company, Rahway, N.J., and 4BrA23187 is a halogenated analog of A23187, available from Signa Chemical Co. St. Louis, Mo.

Effect of Pyrocatechol and SA on Lipid Synthesis by Keratinocytes

It has been reported that the amounts of various classes of lipids change as keratinocytes differentiate through the various layers of the epidermis (Lampe, M. A., M. L. Williams and P. M. Elias. 1983. Human epidermal lipids: characterization and modulations during differentiation. J Lipid Res 24:133–140). The distribution of lipids in the different epidermal layers of normal skin is shown in Table 6. The most significant change is the decrease in polar lipids and increase in neutral lipids that occurs as the keratinocytes progress from the viable cell layers into the stratum corneum. This indicates that a shift from polar lipid to neutral lipid synthesis is associated with differentiation of keratinocytes to corneocytes. The following experiments were thus conducted to determine whether the two compounds tested effected keratinocyte lipid synthesis.

Human squamous carcinoma cells (SCC-9 cell line) were grown to confluent monolayers in 75 $cm^2$ tissue culture flasks at 37° C. in a humidified, 5% $CO_2$ incubator. The cells in each flask were cultured in 15 ml of complete medium, consisting of: Ham's F12 Medium and Dulbecco's Modified Eagle's Medium mixed 1:1 (Gibco), 10% fetal bovine serum (Hyclone), 0.4 µg/ml hydrocortisone, 2 mM L-glutamine, 100 U/ml penicillin, 100 µg/ml streptomycin and 0.25 µg/ml amphotericin B (Sigma). On the day of the experiment the tissue culture medium was removed and replaced with fresh medium containing one of the test compounds. Cells were incubated 24 hours and then scraped from the flask using a rubber policeman. The cells were pelletted by centrifugation at 800×g for 10 minutes. The cell pellet was freeze-dried in a lyophilizer overnight and a dry weight was determined on the material.

The Bligh-Dyer procedure (Bligh, E. G. and W. J. Dyer. 1959. A rapid method of total lipid extraction and purification. Can. J. Biochem. Physiol. 37:911–917), was employed to extract the lipid from the freeze-dried cellular material. More specifically, the procedure used was as follows: the dried material was suspended in 7.5 ml Bligh-Dyer Solution (Chloroform/Methanol/Water at 1:2:0.8 by volume) to dissolve the lipid. The lipid extraction was performed so that the dry weight of the material did not exceed 30 mg/ml of Bligh-Dyer Solution. The material remained suspended in the Bligh-Dyer Solution overnight at 4° C. The material was then homogenized using a Dounce tissue homogenizer with a tight fitting piston. The solution containing the dissolved lipid was combined with an equal amount of Bligh-Dyer Solution that was used to rinse the homogenizer. The combined solutions were then poured through a shark skin filter. The filtrate (organic solution containing the lipids) was dried down under a continuous flow of nitrogen gas and then redissolved in 7.5 ml Bligh-Dyer Solution. To that solution 2 ml of water and 2 ml of chloroform were added. The tube was vortexed to mix the solution and then centrifuged at 1000×g for 10 minutes to separate the organic and aqueous phases. The bottom, organic, chloroform phase was removed and transferred to a separate centrifuge tube. An equal volume of wash solution (Chloroform/Methanol/Water at 1:1:0.9 by volume) was added to the organic phase. The tube was vortexed and centrifuged as above. The bottom phase was collected and the organic solvent was evaporated under nitrogen gas. The dried lipid was dissolved in 0.5 ml warm absolute ethanol and transferred, along with an equal volume of ethanol that was used to rinse the tube, to a microfuge tube. The contents of the microfuge tube were blown dry under nitrogen gas. The dried sample was dissolved in 500 µl of Chloroform/Methanol at 2:1 by volume.

The dry weight of the lipid extract was determined by placing 25 µl of the sample in a small preweighed aluminum pan. The weighing pan was placed on a hot plate set on a low temperature to evaporate the solvent. The pan was cooled for about 15 seconds and then weighed on a Cahn C31 Microbalance. The average weights were determined for each sample by measuring triplicates and the concentration of each sample was calculated.

High-performance thin-layer chromatography (HPTLC) was employed to separate the lipids for analysis. The sample concentration was adjusted to 0.17 µg/ml by adding an appropriate volume of absolute ethanol. An Analtech Silica Gel G 20×20 $cm^2$ HPTLC plate was "cleaned" by running the system I (Methanol/Chloroform/Water at 20:95:1 by volume) solvent to the top of the plate. The plate was air dried and then heat activated in a drying oven at 110° C. for 30 minutes. Samples were applied 1.5 cm from the bottom of the plate in 4 mm wide bands using a Camag Linomat Autospotter. The plate was developed in solvent system I. The solvent front was allowed to migrate 6 cm from the origin. The plate was air dried and developed again in solvent system I. The plate was air dried and then developed in solvent system II(n-Hexane/Diethyl Ether/Glacial Acetic Acid at 8:2:1 by volume). The solvent front was allowed to migrate 8.5 cm above the origin. The plate was air dried and then developed in solvent system III (Petroleum Ether). The solvent front was allowed to migrate 13 cm above the origin. The plate was air dried overnight at room temperature and then immersed for 20 seconds in a solution of 10% (w/v) cupric sulfate hydrate and 8% (w/v) phosphoric acid in water. The plate was drained on a paper towel and "charred" on a heat block at 180° C. for 1 hour. The lipid bands were quantitated, against a set of standards that were run on each plate, by scanning densitometry using a Shimadzu CS9000U, Dual-wavelength, Flying Spot Scanner.

The results of these analyses are presented in Table 8. Compared to the nontreated, control cells, there was a significant reduction in polar lipid, cholesterol sulfate and sphingolipids with increased amounts of neutral lipids synthesized by cells treated with SA. Pyrocatechol also had a marked effect on lipid synthesis causing a complete reduction of sphingolipids, a partial reduction in neutral lipids and cholesterol sulfate and a significant increase in polar lipids. Although the compounds had distinct effects on SCC-9 cell lipid synthesis, in vitro, only SA appeared to induce a shift in lipid metabolism from that of viable keratinocytes to that of corneocytes. Nevertheless, in view of all of the test results contained herein, Pyrocatechol has been demonstrated to be an active keratolytic agent.

TABLE 7

Variations in Lipid Composition During Human Epidermal Differentiation and Cornification.

| Lipid Fraction | S. Basal/Spinosum | S. Granulosum | S. Corneum |
| --- | --- | --- | --- |
| Polar Lipids | 44.5 ± 3.4* | 25.3 ± 2.6 | 4.9 ± 1.6 |
| Cholesterol Sulfate | 2.4 ± 0.5 | 5.5 ± 1.3 | 1.5 ± 0.2 |
| Sphingolipids | 7.3 ± 1.0 | 11.7 ± 2.7 | 18.1 ± 2.8 |
| Neutral Lipids | 51.0 ± 4.5 | 56.5 ± 2.8 | 77.7 ± 5.6 |

*Each datum is presented as percent of total lipid extracted from normal abdominal skin.

The Table is adapted from: Lampe, M. A., M. L. Williams and P. M. Elias. 1983. Human epidermal lipids: characterization and modulations during differentiation. J Lipid Res 24:133–140.

TABLE 8

Effects of Pyrocatechol and SA on the Lipid Composition of SCC-9 cells.

| Treatment[1] | Polar Lipids | Cholesterol Sulfate | Sphingolipids | Neutral Lipids |
| --- | --- | --- | --- | --- |
| Control | 27.65[2] | 22.95 | 11.95 | 37.45 |
| SA | 10.90 | 15.24 | 2.37 | 71.49 |
| Pyrocatechol | 56.30 | 9.80 | 0.00 | 33.90 |

[1]Final concentrations of the designated compounds in the tissue culture medium were: SA, 15 mM and Pyrocatechol, 15 mM.
[2]Each datum is presented as percent of total lipid extracted from each test group.

Further examples of the invention are as follows:

Example A:

| Component | Percentage of formula % (weight/weight) |
| --- | --- |
| Olivetol | 12 |
| Dipropylene Glycol | 88 |

The composition containing 12% (weight/weight) olivetol can be made as follows:

1. The olivetol is placed in a suitable vessel.
2. Propylene glycol is added to the above vessel and the resulting mixture is stirred until a solution was formed.
3. The resulting composition is transferred to appropriate containers for storage at room temperature (22°–27° C).

Example B:

| Component | Percentage of formula % (weight/weight) |
| --- | --- |
| Hydroquinone | 12 |
| Acetone | 10 |
| Dipropylene Glycol | 78 |

The above composition containing 12% (weight/weight) hydroquinone can be made as follows:

1. The hydroquinone is placed in a suitable vessel.
2. Acetone is added to the hydroquinone in the vessel and mixed until a solution was formed.
3. To the mixture formed in step 2, flexible collodion is added to reach the desired final volume and mixed until the entire contents are thoroughly mixed.

4. The composition is transferred to appropriate containers for storage at room temperature (22°–27° C).

Example C:

| Component | Percentage of formula % (weight/weight) |
|---|---|
| Pyrocatechol | 6.0 |
| Balsam fir (Oregon) | 5.0 |
| β-Carotene | 0.05 |
| Acetone | 10.0 |
| Flexible collodion (USP) | qs 100 |

The above composition containing 6% (weight/weight) pyrocatechol can be prepared as follows:

1. Balsam fir (Oregon) and (β-carotene are mixed with acetone in a suitable vessel until thoroughly mixed.

2. Pyrocatechol is added to the mixture formed in step 1 and mixed until dissolved.

3. Flexible collodion is added to the above mixture and stirred until completely mixed.

4. The composition is then transferred to appropriate containers and stored at room temperature 22° C.–27° C.

Preferred ingredients of compositions of the invention fall within the following ranges:

| Component | Percentage of Formula % (weight/weight)) |
|---|---|
| Pyrocatechol or NDGA | 3–24 |
| Balsam Fir (Oregon) | 2–5 |
| β-Carotene, 22% in Vegetable Oil | 0.01–0.05 |
| Acetone | 5–15 |
| Flexible Collodion, USP | 66–90 |

More preferred ingredients of compositions of the invention fall within the following ranges:

| Component | Percentage of formula % (weight/weight) |
|---|---|
| NDGA | 6–20 |
| Ethyl Alcohol (190 proof, USP) | 30–60 |
| Arlasolve 200 Liquid | 15–50 |
| Klucel HXF-NF | 0.3–0.7 |

A most preferred composition of the invention is

| Component | Percentage of formula % (weight/weight) |
|---|---|
| NDGA | 12.00 |
| Ethyl Alcohol (190 proof, USP) | 48.50 |
| Arlasolve 200 Liquid | 39.00 |
| Klucel HXF-NF | 00.50 |

A preferred composition of the invention is

Example D

| Component | Percentage of formula % (weight/weight) |
|---|---|
| Pyrocatechol | 12.00 |
| Acetone | 10.00 |

Example D (continued)

| Component | Percentage of formula % (weight/weight) |
|---|---|
| Flexible collodion (USP) | 72.95 |
| Balsam fir (Oregon) | 5.00 |
| β-Carotene HSE 22% in vegetable oil | 0.05 |

It was made as follows:

1. Pyrocatechol and acetone were mixed in a suitable tank equipped with an explosion proof mixer.

2. Flexible collodion was added and mixed until the pyrocatechol was in complete solution.

3. Balsam Fir Oregon and β-Carotene were added and mixed well until a clear uniform mixture was obtained.

4. The mixture was stored in appropriate containers at room temperature, 22° C.–27° C.

Another preferred composition of the invention is

Example E

| Component | Percentage of formula % (weight/weight) |
|---|---|
| NDGA | 12.00 |
| Acetone | 10.00 |
| Flexible collodion (USP) | 72.95 |
| Balsam fir (Oregon) | 5.00 |
| β-Carotene HSE 22% in vegetable oil | 0.05 |

It was made in the same manner as Example E above except that NDGA was used in place of pyrocatechol.

The most preferred composition of the invention is

Example F

| Component | Percentage of formula % (weight/weight) |
|---|---|
| Part A: | |
| NDGA | 12.00 |
| Ethyl Alcohol (190 proof, USP) | 48.50 |
| Part B: | |
| Arlasolve 200 Liquid[1] | 39.00 |
| Klucel HXF-NF[2] | 00.50 |

[1] Arlasolve 200 Liquid is Arlasolve 200L-Isoceteth-20 which is a polyethylene glycol ether of isocetyl alcohol that conforms generally to the formula $C_{16}H_{33}(OCH_2CH_2)_nOH$ where n has an average value of 20. Other names for this material are PEG-20 Isocetyl Ether; Polyethylene Glycol 1000 Isocetyl Ether; and Polyoxyethylene (20) Isocetyl Ether.
[2] Klucel HXF-NF which is Klucel-Hydroxypropylcellulose which is a propylene glycol ether of cellulose. Another name for this material is 2-hydroxypropyl ether cellulose.

Procedure

1. NDGA was added to the alcohol of Part A and mixed until dissolved.

2. In a container large enough to contain the entire batch, the arlasolve of part B was transferred, and the klucel of part B was added and mixed until well dispersed.

3. While mixing the mixture of step 2, the mixture of step 1 was added and mixed until the gel was uniform and klucel was completely hydrated.

4. The resulting material was stored in a closed container.

What is claimed is:

1. A topical composition comprising a about 2 to about 64% of a compound selected from the group consisting of hydroquinone; olivetol, pyrocatechol and nordihydroguaiaretic acid and a pharmaceutically acceptable carrier material wherein said carrier material is flexible collodion.

2. A composition in accordance with claim 1 which further comprises an enhancer selected from the group consisting of salicylic acid, erucic acid, and propionic acid.

3. A method for the treatment of hyperkeratinizing and hyperproliferative skin diseases and conditions which comprises topically administering a therapeutically effective amount of a composition defined in claim 1.

4. A method for removing corns, calluses and warts which comprises topically administering a therapeutically effective amount of a composition defined in claim 1.

5. A method in accordance with claim 1 wherein the compound is pyrocatechol.

6. A method in accordance with claim 1 wherein the compound is nordihydroguaiaretic acid.

7. A topical composition comprising on a weight/weight basis:

| Percentage of Formula % (weight/weight) | Component |
|---|---|
| 3–24 | Pyrocatechol or Nordihydroguaiaretic acid |
| 2–5 | Balsam Fir (Oregon) |
| 0.01–0.05 | β-Carotene, 22% in Vegetable Oil |
| 5–15 | Acetone |
| 66–90 | Flexible Collodion, USP |

8. A topical composition in accordance with claim 7 comprising:

| Percentage of Formula % (weight/weight) | Component |
|---|---|
| 6.0 | Pyrocatechol |
| 5.0 | Balsam Fir (Oregon) |
| 0.05 | β-Carotene |
| 10.0 | Acetone |
| qs 100 | Flexible Collodion, USP |

9. A topical composition in accordance with claim 7 comprising:

| Percentage of Formula % (weight/weight) | Component |
|---|---|
| 12.00 | Pyrocatechol |
| 10.00 | Acetone |
| 72.95 | Flexible collodion (USP) |
| 5.00 | Balsam fir (Oregon) |
| 0.05 | β-Carotene HSE 22% in vegetable oil |

10. A topical composition in accordance with claim 7 comprising:

| Percentage of Formula % (weight/weight) | Component |
|---|---|
| 12.00 | Nordihydroguaiaretic acid |
| 10.00 | Acetone |
| 72.95 | Flexible collodion (USP) |
| 5.00 | Balsam fir (Oregon) |
| 0.05 | β-Carotene HSE 22% in vegetable oil |

11. A topical composition comprising on a weight/weight basis:

| Percentage of Formula % (weight/weight) | Component |
|---|---|
| 6–20 | Nordihydroguaiaretic acid |
| 30–60 | Ethyl Alcohol (190 proof, USP) |
| 15–50 | Arlasolve 200 Liquid[1] |
| 0.03–0.7 | Klucel HXF-NF[2] |

12. A topical composition in accordance with claim 11 comprising:

| Percentage of Formula % (weight/weight) | Component |
|---|---|
| 12.00 | Nordihydroguaiaretic acid |
| 48.50 | Ethyl Alcohol (190 proof, USP) |
| 39.00 | Arlasolve 200 Liquid[1] |
| 00.50 | Klucel HXF-NF[2] |

\* \* \* \* \*